United States Patent
Kowallik et al.

(10) Patent No.: US 6,752,766 B2
(45) Date of Patent: Jun. 22, 2004

(54) METHOD AND DEVICE FOR SLEEP MONITORING

(76) Inventors: Peter Kowallik, deceased, late of Lengfeld (DE); by Lydia Kowallik, legal representative, Taschenpfad 5, D-97076 Wurzburg-Lengfeld (DE); Wirtz Hubert, Haupstrasse 3, D-04416 Markkleeberg (DE)

( * ) Notice: Subject to any disclaimer, the term of this patent is extended or adjusted under 35 U.S.C. 154(b) by 109 days.

(21) Appl. No.: 10/058,703

(22) Filed: Jan. 28, 2002

(65) Prior Publication Data

US 2002/0169384 A1 Nov. 14, 2002

(30) Foreign Application Priority Data

Jan. 30, 2001 (DE) ......................................... 101 03 973

(51) Int. Cl.⁷ ................................................. A61B 5/00
(52) U.S. Cl. .................................. 600/538; 128/204.23
(58) Field of Search ............................... 600/529–538; 128/204.23

(56) References Cited

U.S. PATENT DOCUMENTS

| | | | |
|---|---|---|---|
| 4,228,806 A | | 10/1980 | Lidow |
| 5,101,831 A | * | 4/1992 | Koyama et al. ............ 600/500 |
| 5,353,788 A | | 10/1994 | Miles |
| 5,551,419 A | * | 9/1996 | Froehlich et al. ...... 128/204.23 |
| 5,645,054 A | * | 7/1997 | Cotner et al. .......... 128/204.23 |
| 6,286,508 B1 | | 9/2001 | Remmers et al. |
| 6,454,719 B1 | * | 9/2002 | Greenhut .................... 600/484 |
| 6,579,242 B2 | * | 6/2003 | Bui et al. ................... 600/537 |
| 6,589,188 B1 | * | 7/2003 | Street et al. ................. 600/538 |

FOREIGN PATENT DOCUMENTS

WO  WO 9309834  5/1993

OTHER PUBLICATIONS

Breath–to–Breath Variability Correlates With Apnea–Hypopnea Index in Obstructive Sleep Apnea; Peter Kowallik et al; Chest 2000; 119:1–9.
Loube D. L. et al., "Indications for positive airway pressure treatment of adult obstructive sleep apnea patients: A consensus statement," Chest, Bd 115, No. 3, Mar. 1999, U. S.

* cited by examiner

Primary Examiner—Robert L. Nasser
(74) Attorney, Agent, or Firm—Ladas & Parry

(57) ABSTRACT

A method of identifying a minimum of one breathing parameter which is characteristic for the breathing status of a sleeping individual comprises the following steps: measurement of the derivative trend with respect to time of a minimum of one variable of state of the cardiovascular system of the individual, which variable recurrently changes with the respiration; determination of breath-to-breath intervals, each of which represents the duration of one breath, from the results of the measurement; and identification of the breathing parameter which is defined by the variability of the breath-to-breath intervals in phases of unobstructed breathing and/or statistical variables derived therefrom. In addition, applications of the method of controlling breathing apparatuses and of signaling breathing statuses of sleeping individuals as well as devices for implementing the methods are described.

19 Claims, 5 Drawing Sheets

METHOD AND DEVICE FOR SLEEP MONITORING

Figure 1:
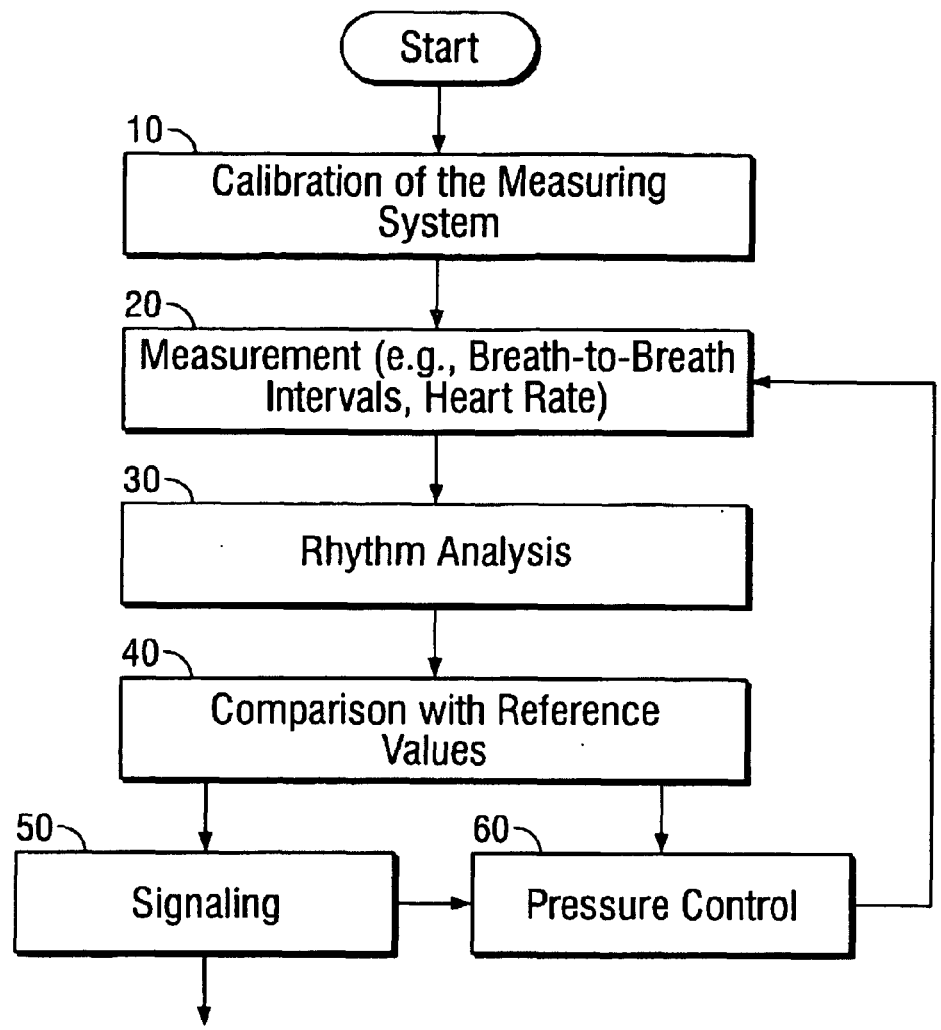

The present invention relates to sleep monitoring methods, in particular methods for identifying breathing parameters that are characteristic to the breathing status of a sleeping individual, methods of controlling breathing apparatuses, and methods of signalizing the breathing status in sleeping individuals. The present invention also relates to devices for implementing said methods, in particular, monitoring devices, breathing apparatuses, pressure generators, and control devices therefor. In addition, the present invention also relates to methods for the detection and treatment of sleep-disordered breathing and devices for implementing said methods.

Sleep-disordered breathing is a widespread disease which can manifest itself in various forms. In many cases, obstructive sleep apnea (OSA) with daytime sleepiness and associated cardiovascular diseases is involved (see, e.g., P. J. Strollo Jr. et al. in N. Engl. J. Med., vol. 334, 1996, page 99). As a result of an increased upper airway resistance (UAR), the upper airways recurrently collapse in the sleeping individual who is suffering from this disease. Even if the obstruction of the upper airways is not complete, increased UAR will still cause clinical symptoms.

Presently, the diagnosis of obstructive sleep apnea involves screening which is able to detect apnea relatively reliably but does not detect so-called hypopnea (breath with reduced flow) with a comparable level of reliability. Measurements of oxygen saturation and of the respiratory flow measured on mouth and nose are carried out. These diagnostic procedures are generally used when a patient complains of daytime sleepiness. But daytime sleepiness is also seen in individuals who experience many interruptions of their sleep (so-called micro-arousals) which occur in the presence of the UAR syndrome (UARS) because the upper airways are narrow without being completely obstructed. The organism must exert considerable pressure to maintain the respiratory flow. Large variations in the pressure in the chest are presumably the cause of micro-arousals and may be responsible for subsequent negative effects on the cardiovascular system. Conventional diagnostic procedures are not able to identify this problem since, due to the high pressure exerted, the respiratory flow is not reduced to a significant extent. The only way to measure the pressure would be to use an intraesophageal balloon which would involve an invasive procedure and cause considerable discomfort to the patient.

The conventional way to detect UARS has been to measure the esophageal pressure and, at the same time, detect micro-arousals (see, e.g., C. Guilleminault et al. in Chest, vol. 104, 1993, page 78 1). But these procedures require a high degree of technical complexity, they are time-consuming and invasive, and they cause the patient discomfort.

It is also known that an increased UAR is associated with changes in the measurable respiration variables of state, e.g., the pressure contour (see J.-J. Hosselet et al. in Am. J. Respir. Crit. Care Med., vol. 157, 1998, page 1461) or the breath cycle lengths (see, e.g., T. Brack et al. in Am. J. Respir. Crit. Care Med., vol. 157, 1998, page 1756). So far, however, this insight has not yet been translated into sleep monitoring applications.

Until now, patients with sleep-disordered breathing problems have been treated with so-called CPAP therapy (CPAP=continuous positive airway pressure). In the treatment with CPAP, the sleeping patient receives continuous positive airway pressure treatment via a nasal mask that is connected to a breathing apparatus (CPAP apparatus).

The disadvantage of CPAP therapy is that the patient is exposed to positive airway pressure over the entire duration of his or her sleep, i.e., for the entire night. This subjects the patient to considerable stress. To reduce this stress as much as possible, a conventional CPAP apparatus is operated at the lowest possible pressure. This, however, entails a risk. In some cases, the operating pressure of the CPAP apparatus may be too low.

Thus, the problem to be solved by the present invention is to make available an improved method of identifying breathing parameters in a sleeping subject, said method is marked especially by the measurement of the simplest possible signal while subjecting the patient to the least stress possible and by expanded applicability, such as is involved in the control of breathing apparatus or in signaling breathing disturbances. Another problem to be solved by the present invention is to provide devices for implementing and using said methods.

These problems are solved by a method, a computer program, or devices having the features described in claims 1, 6, 8, 10, 12, and 13. Useful embodiments and applications of the invention result from the dependent claims.

The basic objective of the present invention is to make available a method of identifying breathing parameters that are characteristic for the breathing status of a sleeping individual, with which method the derivative function with respect to time of at least one variable of status of the cardiovascular system of the patient, which variable undergoes recurrent changes while the patient is breathing, is measured and subjected to a rhythm analysis so as to identify, as breathing parameters, the statistical values of distribution of breath-to-breath intervals in the unobstructed breathing phases or variables derived therefrom (variables which are calculated from the statistical values of the distribution of the breath-to-breath intervals). The breathing parameters to be identified are, e.g., the variability or the so-called kurtosis value of the breath-to-breath intervals under consideration. Any physical or chemical property of the individual that changes parallel in time with the rhythm of the recurrent inspiration and expiration of the individual can be measured as a variable of state of the cardiovascular system. Thus, for example, the flow of air during respiration or the hearth rhythm can be measured. The rhythm analysis of one single variable of state that correlates with the breathing and the statistical analysis of the variability over time of the variable of state in time intervals in which a physiologically normal breathing pattern is present has the advantage that a simple one-channel signal is analyzed by means of which characteristic sleep stages of the individual can be extremely reliably identified.

According to a preferred embodiment of the present invention, a minimum of one of the breathing parameters identified is used to control a breathing apparatus, in particular a pressure generator of a breathing apparatus. Surprisingly, the inventors discovered that the breathing parameters identified according to the present invention are suitable for controlling the operating status of breathing apparatuses, in particular with regard to the level of the auxiliary pressure to which the patient is subjected, e.g., to avoid OSA or UAR syndromes. Thus, the subject matter of the present invention concerns especially a control procedure for breathing apparatuses, with which procedure a pressure generator of the breathing apparatus is controlled as a function of the breathing parameters and the value of the generated pressure is set. This control procedure has the advantage that the substantially known CPAP treatment can be carried out in a less stressful manner by increasing the pressure only when a dangerous breathing situation arises. As a result, the discomfort for the patient is considerably reduced.

According to another preferred embodiment of this invention, a minimum of one of the breathing parameters is used to control a sleep monitoring apparatus which is designed to signal and/or register breathing disturbances. It was discovered that by comparing the breathing parameters identified according to the present invention to reference values of healthy individuals, these parameters can be suitably used for supplying reliable data on the intermittent obstruction or occlusion of the upper airways of a sleeping individual. Thus, the subject matter of the present invention also concerns a method of signaling and/or registering interruptions of sleep caused by breathing disturbances. Preferably, signaling is done with visual signals (LED display or screen display, logging printer) or acoustic signals (alarm).

Another subject matter of the present invention concerns the method of the above-mentioned rhythm analysis of measured variables of state of the cardiovascular system of an individual, which recurrently change over time in correlation with the respiration and, in particular, computer programs tools for implementing such methods.

Devices according to the present invention for implementing the methods mentioned above include, in particular, breathing apparatuses with controllable pressure generators and sleep monitoring devices with signaling devices that are chosen on the basis of the specific application. The sleep monitoring device as such can be part of the breathing apparatus. The pressure generator and/or the signaling device is/are operated as a function of the breathing parameters identified according to the present invention and predetermined reference values. The breathing apparatus forms a feedback control circuit in which the variable of state of the cardiovascular system is continuously measured, analyzed, and compared to the reference values. The pressure generator is set as a function of the result of the comparison to the reference values. Accordingly, a device according to the present invention comprises a measuring device, a processor circuit, and an actuating device for the pressure generator.

This invention has the following advantages. The breathing parameters identified according to the present invention make it possible monitor sleep reliably and reproducibly. Simple signal processing is provided. The stress on the individual caused by the measured data acquisition is low. Breathing and/or sleep monitoring apparatuses can be designed for use in a clinical environment (sleep laboratory) or for personal use by individuals. The invention can be universally implemented for use on any patient, in particular regardless of the age of the patient. According to the present invention, a simple and easy method is provided which makes it possible to detect the UAR symptom. In the presence of symptoms which are similar to those suffered by patients with OSA, conventional means could detect an UAR symptom only by means of complicated measurements of the esophageal pressure, something that is avoided when the method according to the present invention is used.

Figure 2:
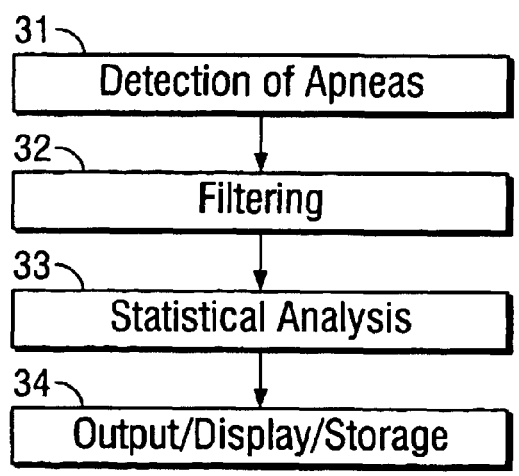
Figure 3A:
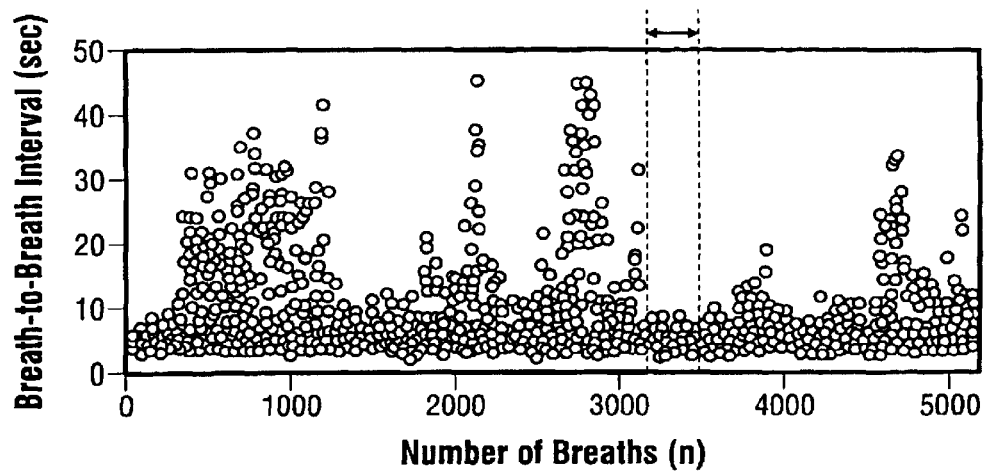
Figure 3B:
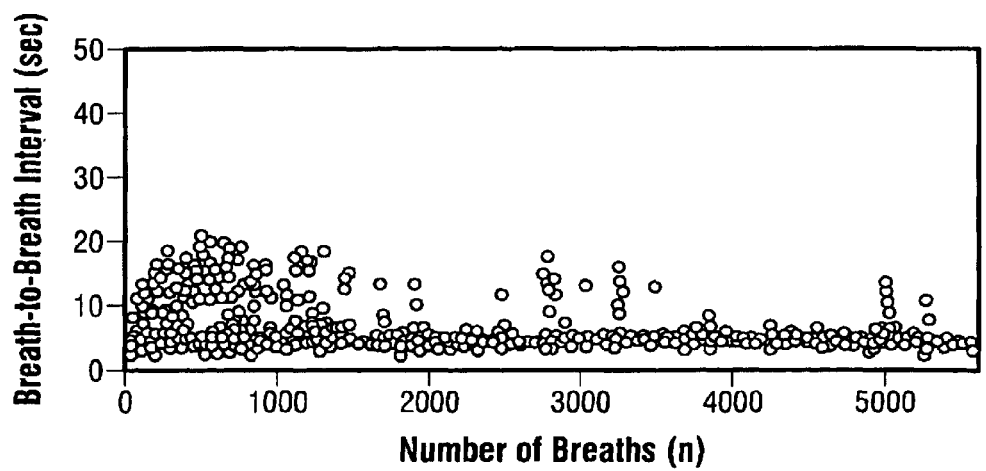
Figure 4C:
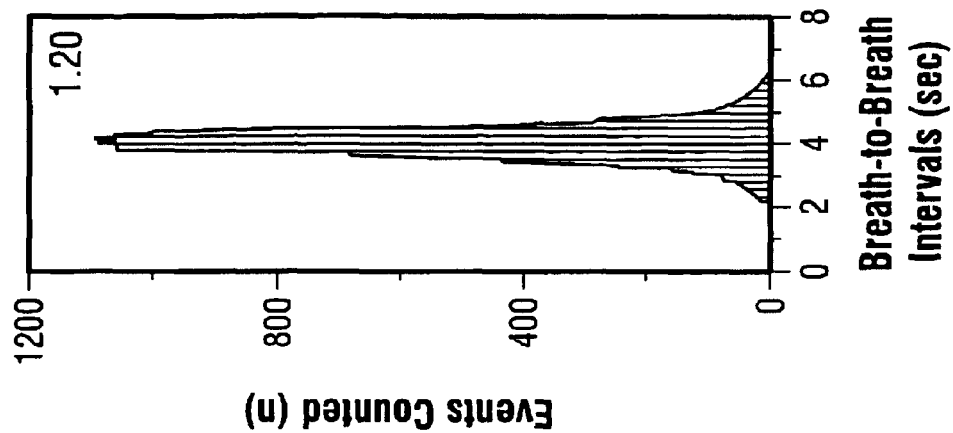
Figure 4B:
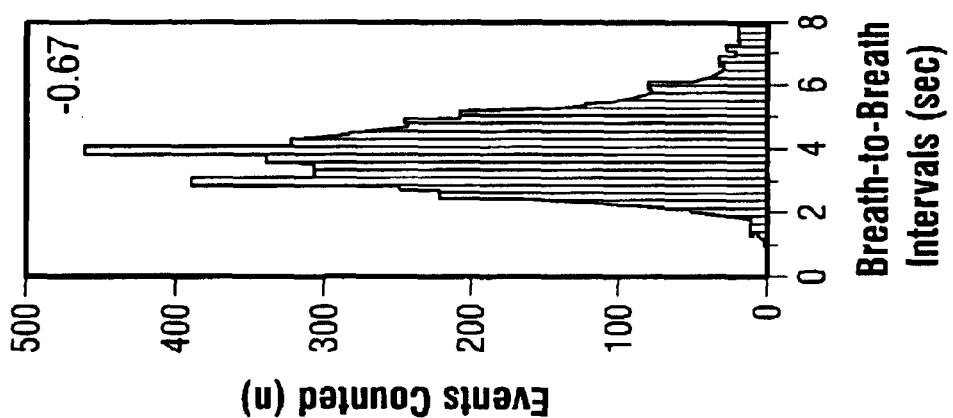
Figure 4A:
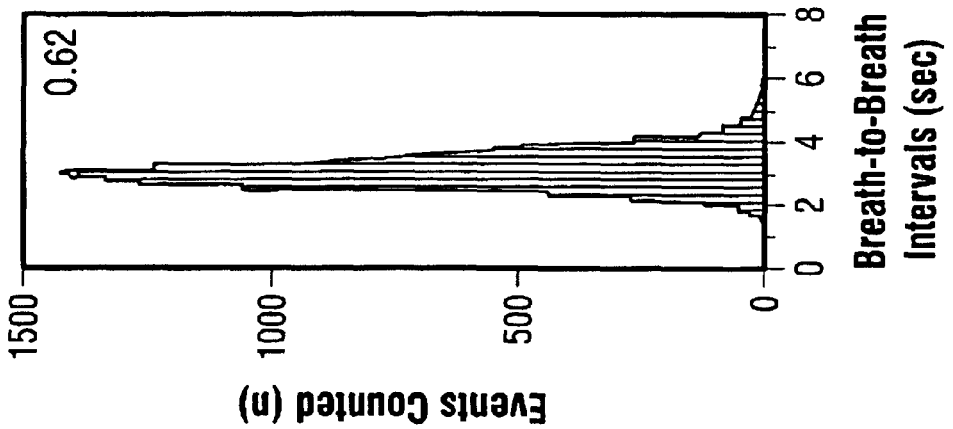
Figure 5A:
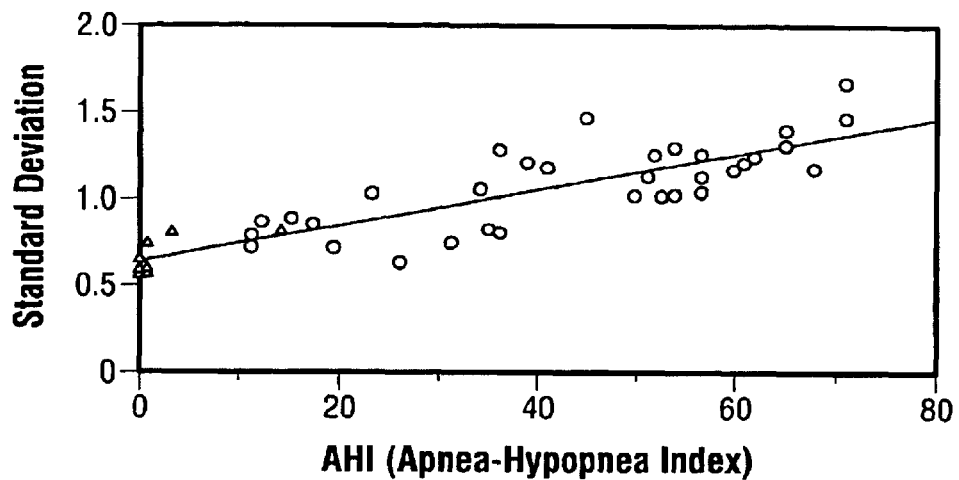
Figure 5B:
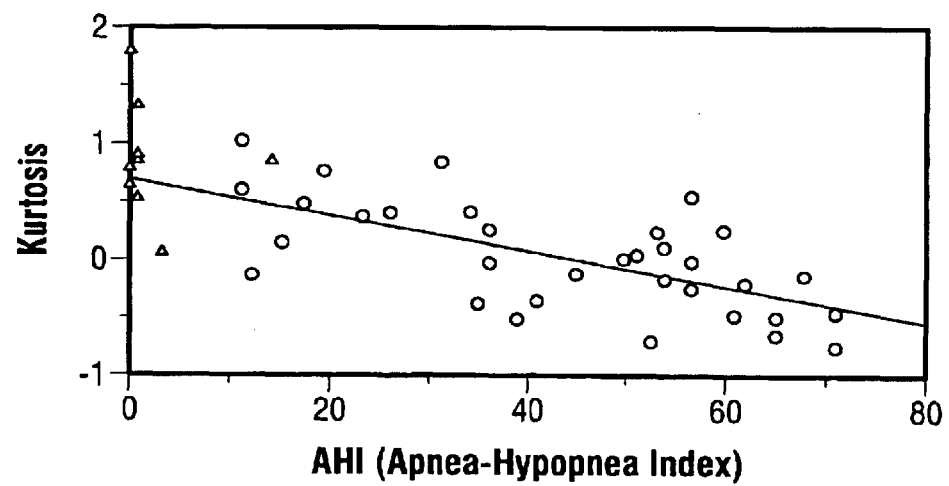
Figure 6:
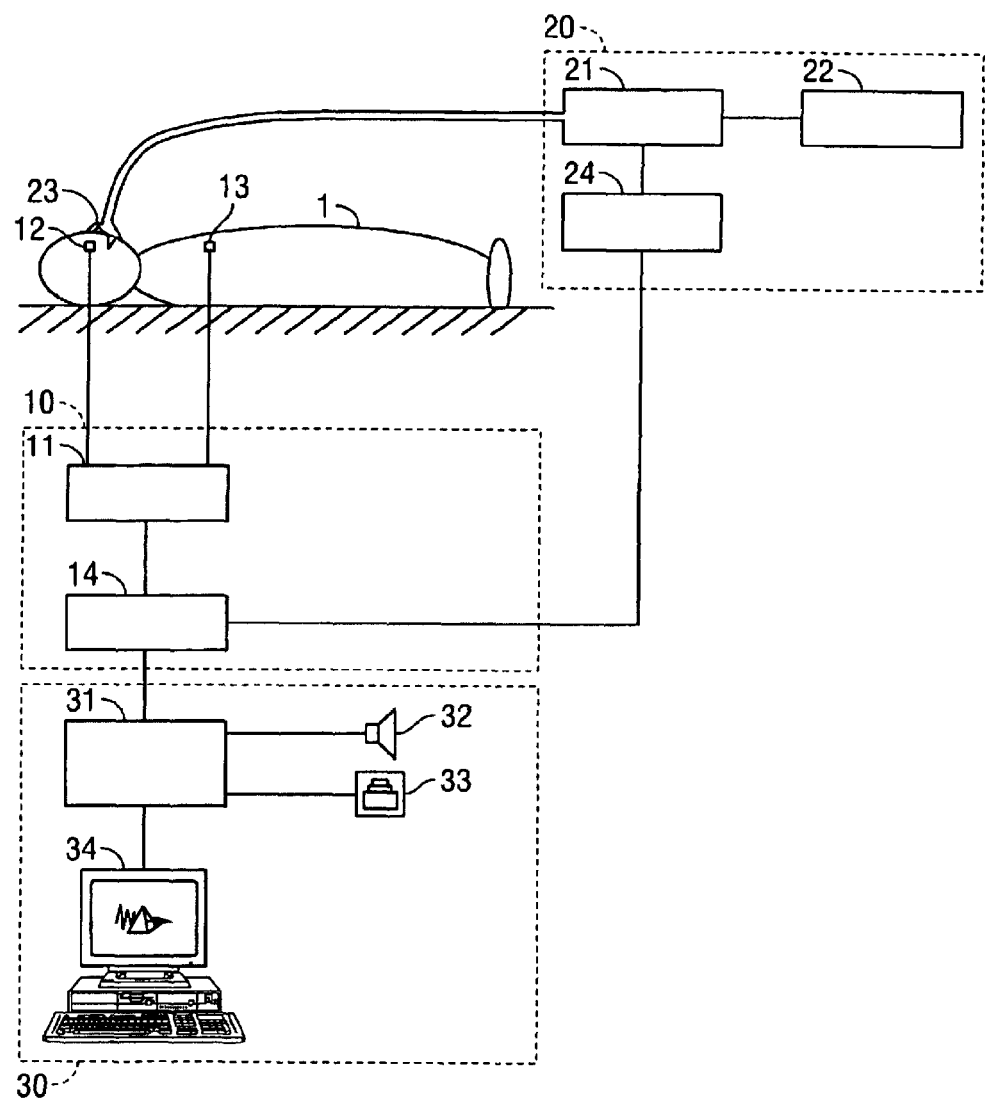

Other details and advantages of the invention will be described with reference to the attached drawings. As can be seen:

FIG. 1 is a flow chart which illustrates the identification of breathing parameters according to the present invention, FIG. 2 is a flow chart which illustrates details of the rhythm analysis according to the present invention, FIGS. 3 through 5 show curves with measured and analytical results obtained with the methods according to the present invention, and FIG. 6 is a diagrammatic overview of an embodiment of breathing and/or sleep monitoring devices according to the present invention.

EMBODIMENTS OF METHODS ACCORDING TO THE PRESENT INVENTION

FIG. 1 is an overview of various possibilities of how to implement and utilize the detection of breathing parameters according to the present invention. The important steps of parameter detection control include measurement 20 of at least one variable of state and rhythm analysis 30. A comparison 40 of the breathing parameters detected to reference values, followed by signaling 50 and/or pressure control 60, are preferred applications of this invention. Calibration 10 which is carried out at the beginning of the procedure is a facultative feature of the invention which, depending on the application, can be carried out one time only or, subject-specifically, repeatedly.

Measurement 20 comprises the metrological recording of the derivative trend with respect to time of at least one variable of state of the cardiovascular system of the individual, which variable changes in correlation with the respiration. For example, the respiratory flow or the cardiac activity is measured directly or indirectly. The respiratory flow is measured by means of a respiratory flow sensor, e.g., indirectly by means of a thermistor. The cardiac activity is determined by means of a high-resolution long-term recording of an electrocardiogram (ECG). The R-R intervals in the ECG are recorded, and based on these, the derivative trend with respect to time of the breaths is reproduced. Based on the measured derivative trend with respect to time of the variable of state, the breath-to-breath intervals are determined as a function of time, and possibly the intensity of the breaths (respiratory flow) is assessed.

The measurement of the breath-to-breath interval on the basis of the respiratory flow signals is preferably carried out by detecting the minima of the respiratory flow signals and by determining the time interval between these minima. The interval between two minima is used as the value for the breath-to-breath interval. Alternatively, the value for the breath-to-breath intervals can also be determined on the basis of the time interval between the zero values of the respiratory flow or the maxima. Because the minima detection is more reliable, which is especially important for the subsequent statistical analysis (see step 30), it is to be preferred.

In FIG. 3, the measured respiratory intervals of an individual A with obstructive sleep apnea and a treated individual B (see below) are compared. The breath-to-breath intervals were recorded over a period of approximately 8 h. Within a typical breath-to-breath interval of approximately 6 sec, approximately 5,000 breaths are counted. Frequently, respiratory intervals lasting far longer than 10 sec are encountered, in particular in individual A with obstructive sleep apnea. Respiration is interrupted for up to 45 sec. In rhythm analysis 30, the derivative trend with respect to time of the variable of state measured is processed and a statistical analysis is carried out. Details of these steps are diagrammatically illustrated in FIG. 2. This procedure for processing and analyzing measured variables shown in FIG. 2 is also a subject matter of the present invention.

First, the rhythm analysis step 30 optionally involves apnea detection 31 (not absolutely required), subsequently filtering 32 of the unobstructed respiration, next statistical analysis 33, and finally an output, display and/or storage 34 of the breathing parameters detected in step 33.

In apnea detection step 31, all breath-to-breath intervals that last longer than a predetermined apnea threshold value are determined. This threshold value is, e.g., 10 sec. Based on the chronological density of the apnea episodes, the apnea index AI is calculated. The apnea index equals the number of apnea episodes per hour. In addition, the mean value and the standard deviation over the duration of all apnea episodes are calculated.

Step 31 may also provide for the detection of hypopnea with the help of the apnea-hypopnea index AHI. A hypopnea episode is present if the respiratory flow determined during the measurement or estimated on the basis of the measurement drops below a certain limit (e.g., 50%) for a duration longer than a predetermined hypopnea threshold value (e.g., 10 sec) and is associated with a minimum decrease in the oxygen saturation (e.g., 4%). The AHI results as the total number of apnea and hypopnea episodes per hour.

Filtering 32 aims at determining all breaths taken during a period of unobstructed respiration. All breath-to-breath intervals are compared to a predetermined filter value. The values of the breath-to-breath intervals that are shorter than the filter value are considered normal unobstructed respiration. The filter value is predetermined, for example, as an absolute value (e.g., 10 sec, see step 31). In FIG. 3 (upper portion), the double arrow marks a longer time period in which unobstructed respiration takes place.

In step 33, the filtered breaths with normal unobstructed respiration are subjected to a statistical analysis. The statistical analysis is predicated on the presence of a sufficient number of measured values. Fortunately it was found that the invention yields reliable results after only short measuring times in the minute range, e.g., within approximately 10 min. In the statistical analysis, not only consecutive groups of breaths are considered but also breaths which are part of different groups of breaths that are separated by apnea episodes. In particular, the mean value and the standard deviation of the breath-to-breath intervals are determined. In addition, it is useful to define a normal breathing range which covers all breath-to-breath intervals with a duration within ±50% of the mean value. This ensures that the result of the evaluation is not falsified by isolated cases of large variations in the measurement ("outliers"). All breath-to-breath intervals which fall within the normal range are then used as so-called normal intervals to calculate the standard deviation and the kurtosis value. Alternatively, however, the statistical variables can also be determined on the basis of all breath-to-breath intervals with unobstructed respiration. The kurtosis value δ (or the so-called excess value) is defined as follows:

$$\delta = \left[ n \sum_{i=1}^{n} (x_i - \bar{x})^4 \bigg/ \left( \sum_{i=1}^{n} (x_i - \bar{x})^2 \right)^2 \right] - 3$$

where x=the mean value of the n (n=natural number) counted measured values $x_i$ included in the distribution.

The kurtosis value of a normal distribution is zero. A positive kurtosis value indicates a sharper distribution peak compared to the normal distribution; a negative kurtosis value, on the other hand, indicates a flattened distribution.

The inventors discovered that especially the kurtosis value and the standard deviation of the breath-to-breath intervals as the breathing parameters defined according to the present invention correlate with the AHI value and thus are characteristic for the sleep stage of the individual. The statistical evaluation 33 takes place using substantially known statistical procedures and program tools. In step 34, the breathing parameters defined (kurtosis value and/or standard deviation) are read out for further processing, displayed (e.g., visually on a screen or printed out) and/or stored. In addition, to provide for an adaptation of the breathing parameters to subsequent steps, provision can be made to convert the values.

FIGS. 4 and 5 illustrate the statistical evaluation 34 on the basis of an example. FIG. 4 shows the distribution of the included breath-to-breath intervals for a healthy individual A, an OSA patient B, and a treated OSA patient C. The breathing pattern of the healthy individual A is very uniform. No apnea episodes are present. The standard deviation for the duration of all (unobstructed) breaths is small. The distribution of the normal intervals is very narrow. The kurtosis is correspondingly greater than 0 (in this case, e.g., 0.62). By contrast, the breathing pattern of OSA patient B is characterized by frequent discontinuations (see also FIG. 3, upper portion). It can be seen that even the unobstructed breathing of the OSA patient is different. The standard deviation of the intervals of normal length is increased. In addition, the frequency distribution of the intervals of normal length is different, which can be seen on comparison of the left and center portions of FIG. 4. The kurtosis value is significantly lower (e.g., −0,67).

As illustrated in FIG. 5, there is a significant positive correlation between the standard deviations of the unobstructed breath-to-breath intervals and the AHI values (upper portion of FIG. 5) and a significant negative correlation between the AHI values and the kurtosis values of the breath-to-breath frequency distributions (lower portion of FIG. 5). As can be seen, the standard deviations increase (greater variability of the breath-to-breath intervals) as the AHI value increases, i.e., in particular as the number of apnea episodes increases relative to the hypopnea episodes), and the kurtosis values decrease (increasing deviation of the frequency distribution of the intervals of normal length of a normal distribution). It is on this surprising discovery that the applications of the procedure according to the present invention for the artificial ventilation and/or for sleep monitoring which will be described below with specific reference to steps 40, 50, and 60 in FIG. 1 are based.

The correlations mentioned between the breathing parameters identified according to the present invention and the sleep stages, which are characterized by an increased AI or AHI value, make it possible, solely on the basis of a comparison (step 40 in FIG. 1) with the reference value, to signal the sleep stage and/or to set a breathing apparatus. A method of analyzing sleep stages by means of defining a minimum of one breathing parameter and comparing it to a minimum of one reference value is also a subject matter of this invention. During comparison 40, the presently measured value of the breathing parameters is compared to a predetermined stored reference value. If, for example, the standard deviation is greater than the reference value or if the kurtosis value falls below the reference value, an actuating signal is generated, with which the signaling 50 and/or pressure control 60 steps are started. The reference value used is a previously stored universal reference value (absolute values of healthy individuals measured).

If the actuating signal is generated in step 40, an acoustic signal, a display, or a printed protocol is generated in step 50. This signal is addressed to an operator of the control device, e.g., in the sleep laboratory, or to the individual him- or herself.

The analytical procedure according to the present invention with the possibility of signaling sleep stages with obstructed respiration can be implemented by means of a device according to the present invention (see below) and/or a computer program.

The advantage of controlling the pressure generator of a breathing apparatus as a function of the breathing parameters identified is shown in FIG. 3 (lower portion) and in FIG. 4 (right portion). An OSA patient is connected via a nasal mask to a breathing apparatus (CPAP apparatus). Actuating or increasing the excess pressure administered to the patient as a function of the result obtained in comparison step 40 results in a considerable reduction of the number of apnea episodes as well as in a considerably shorter duration of such episodes (see FIG. 3) and in a decreased variability of unobstructed respiration and a marked increase in the kurtosis value (see treated patient C in FIG. 4).

EMBODIMENTS OF DEVICES ACCORDING TO THE PRESENT INVENTION

FIG. 6 is a diagrammatic representation which shows the components of a breathing and sleep monitoring device according to the present invention. According to modified embodiments of the present invention, an apparatus solely comprising a monitoring and breathing apparatus can be designed. FIG. 6 comprises a control device 10, a breathing apparatus 20, and a signaling device 30.

Control device 10 comprises a measuring unit 11 which is connected to the patient via sensors 12, 13, a processor circuit 14, and an actuating device 15. Any breath transducer capable of measuring breath-to-breath intervals (e.g., nasal pressure transducers, pneumotachographs, CPAP flow/pressure sensors, thermoelements, acoustic sensors, etc.) can be used as a sensor. Sensors 12, 13 may be, for example, thermistors or an ECG electrode layout. The measuring device is provided so as to be able to implement steps 10 and 20 mentioned above; it comprises a substantially known device for measuring the respiratory flow and/or an ECG apparatus. The results measured are transmitted to process circuit 14 which is designed to implement the above-mentioned steps of rhythm analysis 30. Process circuit 14 can be, for example, a microprocessor of a computer in which rhythm analysis 30 is carried out with the computer program mentioned. Alternatively, however, it is also possible to provide for a circuit-based conversion of the rhythm analysis 30 with comparator and filter circuits for implementing the above-mentioned steps 31 and 32 and computational circuits for statistical analysis 33. Furthermore, the process circuit can be connected with a storage unit, display devices and/or output devices. Depending on the application, process circuit 14 can also be designed so as to be able to implement comparison step 40 and to provide the actuating signal when obstructed respiration is detected. The actuating signal is sent to actuating device 24 which activates breathing apparatus 20.

Breathing apparatus 20 comprises a substantially known CPAP device 21 with a pressure generator, optionally an additional control circuit 22, and actuating device 24. CPAP device 21 is connected to patient 1 via a tubular connection and a nasal and/or oral mask 23. On generation of the actuating signal by process circuit 14, the pressure of CPAP device 21 is increased. The increase first takes place at a predetermined pressure interval (e.g., 1 mbar) which can be further increased as the measurements continue. Vice versa, provision can also be made for the decrease of the pressure. The CPAP control may also provide for a short-term (e.g., in time intervals of approximately 10 min, depending on the breathing parameters identified) or a longer-term change in pressure (e.g., optimization from one night to the next).

Signaling device 30 also comprises an actuating device 31 with which a sound generator 32, a printer 33 and/or a display unit 34 is activated by the process circuit 14 as a function of the actuating signal.

Signaling device 30 is preferably used to generate an optical signal or an acoustic signal if the sleep monitoring device detects a UAR symptoms as a function of the breathing parameters defined according to the present invention.

Other subject matters of the present invention also concern a diagnostic procedure for detecting sleep stages with breathing disturbances as well as a procedure for the treatment of sleep-disordered breathing with the use of breathing parameters defined according to the present invention.

The characteristics of the present invention as disclosed in the preceding description, the drawings and the claims, both individually and in any combination, may play an important role in the implementation of the present invention in its various embodiments.

What is claimed is:

1. A method of detecting a minimum of one breathing parameter that is characteristic for the breathing status of a sleeping individual, comprising the following steps: measuring of the derivative trend with respect to time of a minimum of one variable of state of the cardiovascular system of the individual, which variable changes recurrently during respiration, determining of breath-to-breath intervals, each of which represents the duration of one breath, based on the results of the measurement, and determining of the breathing parameter which is identified by the variability of the breath-to-breath intervals in phases of unobstructed breathing and/or statistical variables derived therefrom.

2. The method as in claim 1 in which the breathing parameter determined is the standard deviation and/or the kurtosis value of breath-to-breath intervals.

3. The method as in claim 1, in which the variable of state measured is the respiratory flow and/or an ECG signal.

4. The method as in claim 1, including subjecting the measured breath-to-breath intervals to a time filter to determine the phases of unobstructed breathing.

5. The method as in claim 1, including comparing at least one breathing parameter determined is to a reference value and an actuating signal for a breathing and/or signaling device is generated as a function of this comparison.

6. The method of controlling a breathing apparatus as in claim 1, including controlling a pressure generator of the breathing apparatus is a function of at least one breathing parameter which was determined using a method described in accordance with the recited steps.

7. The method as in claim 6 including generating an increased breathing pressure by using the pressure generator if at least one breathing parameter is characteristic for the presence of a breathing disturbance.

8. A method of signaling and/or registering a breathing stage, including generating an actuating signal for triggering a signaling device as a function of at least one breathing parameter which was identified by the variability of the breath-to-breath intervals in phases of unobstructed breathing and/or statistical variables derived therefrom.

9. The method as in claim 8, in which the signaling device generates acoustic signals or visual signals, in particular a light-emitting diode display and/or screen display, or activates a logging printer.

10. A method of analyzing the rhythm of measured variables of state of the cardiovascular system of an individual, which variables change over time in correlation with the respiration, comprising the following steps:

time filtering of measured breath-to-breath intervals with determination of all breath-to-breath intervals which are shorter than a predetermined threshold value and in which respiration is unobstructed, statistically analyzed the filtered breath-to-breath intervals, with the determination of statistical variables which are characteristic for the frequency distribution of the duration of the breath-to-breath intervals, and outputting, displaying and/or storing of the determined statistical variables as breathing parameters.

11. The method as in claim 10, in which the statistical variables comprise the standard deviation and/or the kurtosis value of the breath-to-breath intervals in phases of unobstructed breathing.

12. A computer program embodied on a computer readable medium for implementing a method of detecting a minimum of one breathing parameter that is characteristic for the breathing status of a sleeping individual in accordance with claim 1.

13. A device for artificially ventilating a patient and/or for signaling sleep stages, comprising:

a control device which is designed to detect a minimum of one breathing parameter from measured breath-to-breath intervals which is characteristic for the breathing status of a sleeping individual and which comprises a comparator for comparing at least said one breathing parameter to a reference value, with the control device being designed to generate an actuating signal as a function of the result of the comparison, and a breathing apparatus and/or a signaling device which can be controlled with the actuating signal.

14. The device as in claim 13, in which the breathing device comprises a pressure generator which can be controlled by means of the actuating signal.

15. The device as in claim 13, in which the breathing device comprises a CPAP device.

16. The device as in claim 13, comprising a measuring device which is connected to the individual via sensors and which is designed so as to allow the measurement of the derivative trend with respect to time of at least one variable of state of the cardiovascular system of the individual, which variable recurrently changes with the respiration.

17. The device as in claim 16, in which the sensors comprise a thermistor (12) and/or an ECG electrode layout.

18. The device as in claim 13, in which the signaling device comprises a sound generator, a printer and/or a display unit.

19. The method of use of a device as claimed in claim 13 for the diagnosis or treatment of sleep-disordered breathing.

* * * * *

UNITED STATES PATENT AND TRADEMARK OFFICE
CERTIFICATE OF CORRECTION

PATENT NO. : 6,752,766 B2
DATED : June 22, 2004
INVENTOR(S) : Dr. Peter Kowallik et al.

It is certified that error appears in the above-identified patent and that said Letters Patent is hereby corrected as shown below:

<u>Title page,</u>
Item [76], Inventors, delete "Wirtz Hubert" and insert -- Hubert Wirtz --.

Signed and Sealed this

Sixth Day of September, 2005

JON W. DUDAS
*Director of the United States Patent and Trademark Office*